(12) United States Patent
Knoll-Ewers

(10) Patent No.: US 6,482,147 B2
(45) Date of Patent: Nov. 19, 2002

(54) PENILE PROSTHESIS WITH A MAGNETIC DEVICE INCORPORATED THEREIN

(76) Inventor: Deborah Knoll-Ewers, 340 Brighton St., Hercules, CA (US) 94547

( * ) Notice: Subject to any disclaimer, the term of this patent is extended or adjusted under 35 U.S.C. 154(b) by 20 days.

(21) Appl. No.: 09/767,069

(22) Filed: Jan. 23, 2001

(65) Prior Publication Data

US 2002/0099262 A1 Jul. 25, 2002

(51) Int. Cl.$^7$ ............ A61F 5/00; A61N 2/00
(52) U.S. Cl. ............ 600/38; 600/9
(58) Field of Search ............ 600/30–40, 9–13, 600/434; 128/833, 897; 416/3; 29/607; 335/302

(56) References Cited

U.S. PATENT DOCUMENTS

| | | | |
|---|---|---|---|
| 2,844,363 A | * 7/1958 | Clark | 416/3 |
| 3,984,708 A | 10/1976 | Holmlund et al. | 310/30 |
| 3,996,933 A | * 12/1976 | Gutnick | 128/833 |
| 4,258,705 A | * 3/1981 | Sorensen et al. | 600/30 |
| 4,318,396 A | * 3/1982 | Finney | 600/40 |
| 4,411,261 A | 10/1983 | Finney | |
| 4,584,994 A | 4/1986 | Bamberger et al. | |
| 4,647,891 A | * 3/1987 | Hughes | 29/607 |
| 4,664,100 A | * 5/1987 | Rudloff | 600/40 |
| 4,722,327 A | 2/1988 | Harvey | |
| 4,791,917 A | * 12/1988 | Finney | 600/40 |
| 5,230,694 A | * 7/1993 | Rosenblum | 600/40 |
| 5,803,897 A | 9/1998 | Mooreville | 600/40 |
| 5,851,185 A | * 12/1998 | Berns | 600/434 |
| 5,905,425 A | * 5/1999 | Dalby et al. | 335/302 |
| 6,085,751 A | * 7/2000 | Taparia | 128/897 |
| 6,357,446 B1 | * 3/2002 | Taparia | 128/897 |

OTHER PUBLICATIONS

Xandria.Com, Sex Education Life Pleasure, Magnetic Massager Acupressure Kit, 1997–2002, LRC, Inc.*

* cited by examiner

Primary Examiner—Eric F. Winakur
Assistant Examiner—Nikita Veniaminov
(74) Attorney, Agent, or Firm—Goldstein & Lavas, P.C.

(57) ABSTRACT

A sexual aid device substantially the size and shape of an adult male penis. The device has a head portion, an elongated shaft, and a base portion. The device also has an outer covering that is constructed from a resilient material to simulate the look and feel of an erect adult penis. A magnetic element is housed within the device, within its cavity. The magnet is cylindrical in shape, one piece, and extends continuously substantially from the head portion downward to the base. Since it lies below the outer covering, the magnet would never come into direct contact with any portion of the human body. The actual thickness of the outer covering should be minimized while maintaining sufficient thickness to ensure comfort for the user.

4 Claims, 2 Drawing Sheets

PENILE PROSTHESIS WITH A MAGNETIC DEVICE INCORPORATED THEREIN

BACKGROUND OF THE INVENTION

The invention relates to a sexual aid device with a magnetic element incorporated therein. In particular, the invention is a sexual aid in the form of an adult erect penis, which may enhance the user's sexual experience and health by utilizing the theories of magnetic therapy.

Magnetic therapy dates back to ancient Greece and Egypt, although it has only recently been recognized as a form of rehabilitation and pain management. The premises of the therapy is to use magnetic fields to increase blood circulation in injured tissue and encourage healing by stimulating the nervous system.

Since magnets exert a powerful attraction to the iron content in the blood, this force penetrates the outer layers of skin, muscle and fatty tissue to the capillaries that feed directly into the bloodstream. By attracting iron and other inorganic molecules, circulation in the area exposed is increased. The combined effect is the improvement of blood circulation in the designated region of the human body.

Studies have indicated that through the magnets' natural effect on charged particles in the blood, they help vessels expand, allowing a larger quantity of nutrient-rich blood to flow into an area for faster healing and growth. Small eddy currents occur in the blood stream, contributing to the widening of the blood vessels, thus allow more blood to pass through.

Although the use of magnet therapy primarily has been explored for its healing qualities, particularly in conjunction with muscle aches and soft tissue damage, its uses do not end there. Sexual stimulation, principally in women, may be increased with the use of magnets. The woman's vaginal tissue is loaded with blood vessels. When sexually aroused, these blood vessels become engorged with blood and press against the tissue, forcing natural tissue fluids through the walls of the vagina. Bringing a women's genital region into contact with a magnet device would cause the vessels to further expand, thereby increasing the pleasure experienced by a woman during sexual stimulation.

Numerous sexual aid devices are available, however none seem to combined a magnetic device into the device for the purpose of increasing sexual pleasure in women. By way of example, U.S. Pat. No. 5,803,897 to Mooreville et al. discloses a penile prosthesis with a pump rotor directly actuated by rotating magnetic fields.

U.S. Pat. No. 4,722,327 to Harvey discloses a therapeutic apparatus designed for sexual stimulation, including an artificial penis coupled with a housing, said housing used to operate and control the movements of the penis.

U.S. Pat. No. 4,584,994 to Bamberger et al. discloses an electromagnetic implant for use in impotent males to achieve erection. The device is implanted in the scrotum.

U.S. Pat. No. 3,984,708 to Holmlund et al. discloses a electromagnetic tactile stimulator used to impart vibratory impulses of varying intensity to a subject's skin to enhance lost senses, such as sight or sound.

U.S. Pat. No. 4,411,261 to Finney shows a semi-rigid penile implant, employing two magnets to hold the implant in an erectile position.

While these units may be suitable for the particular purpose employed, or for general use, they would not be as suitable for the purposes of the present invention as disclosed hereafter.

SUMMARY OF THE INVENTION

In the view of the foregoing disadvantages inherent in the known types of sexual aids now present in the prior art, the present invention provides an improved penile prosthesis device. As such, the general purpose of the present invention, which will be described subsequently in greater detail, is to provide a new and improved sexual aid device with a magnet incorporated therein.

The present invention essentially comprises a sexual aid device substantially the size and shape of an adult male penis. The device has a head portion, an elongated shaft, and a base portion. It also has an outer covering within which a magnetic element is housed.

There has thus been outlined, rather broadly, the more important features of the invention in order that the detailed description thereof that follows may be better understood, and in order that the present contribution to the art may be better appreciated. There are, of course, additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

It is therefore an object of the present invention to provide a new and improved penile prosthesis with a magnet incorporated therein which has all the advantages of the prior art sexual aids and none of the disadvantages.

It is another object of the present invention to provide a new and improved sexual aid device with a magnet incorporated therein which may be easily and efficiently manufactured and marketed.

It is a further object of the present invention to provide a new and improved sexual aid device with a magnet incorporated therein which is of durable and reliable construction.

An even further object of the present invention is to provide a new and improved penile prosthesis with a magnet incorporated therein which is susceptible of a low cost of manufacture with regard to both materials and labor, and which accordingly is then susceptible of low prices of sale to the consuming public, thereby making such sexual aid device economically available to the buying public.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
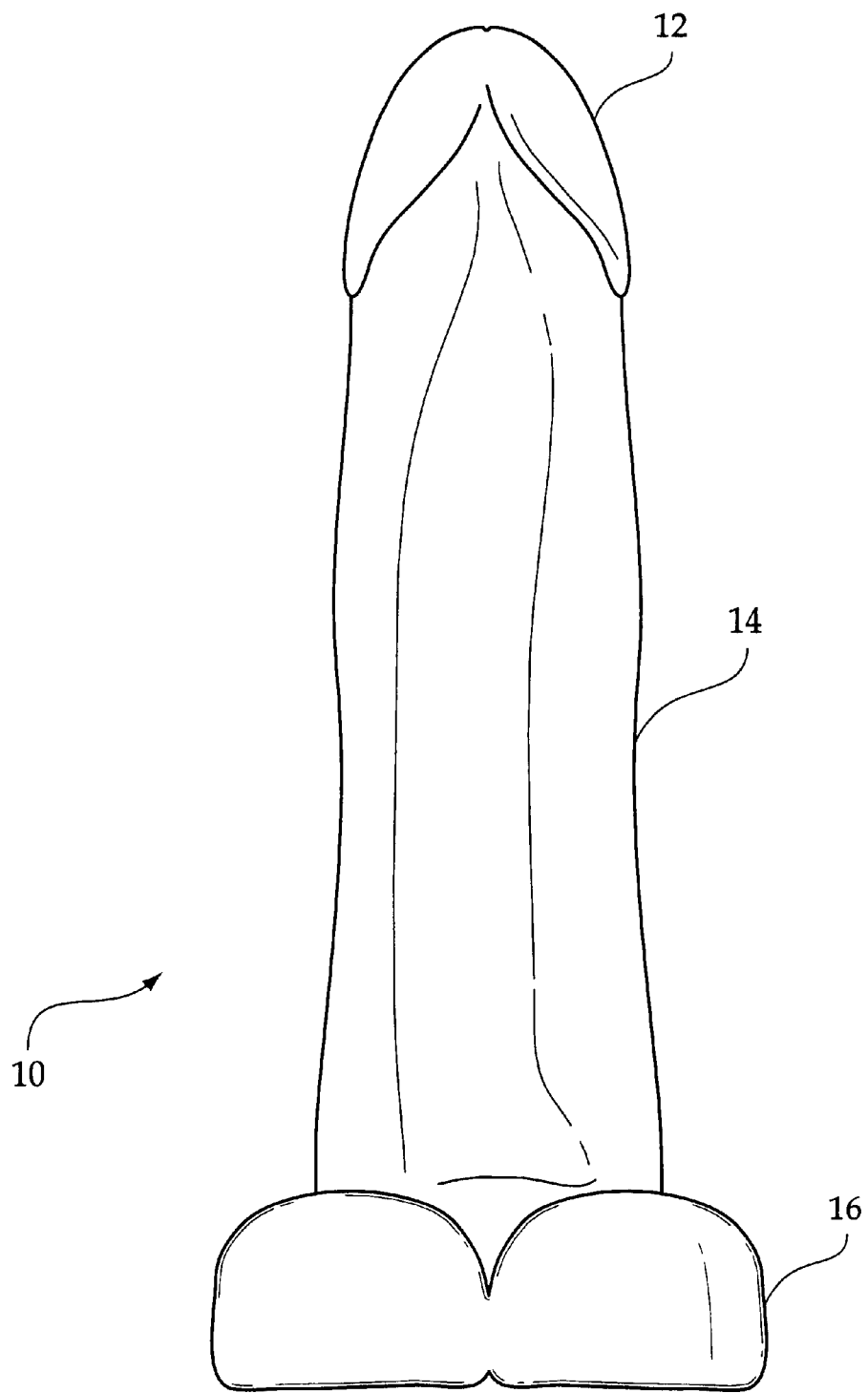
FIG. 1 is a perspective view of the sexual aid device with a magnet incorporated therein.
Figure 2:
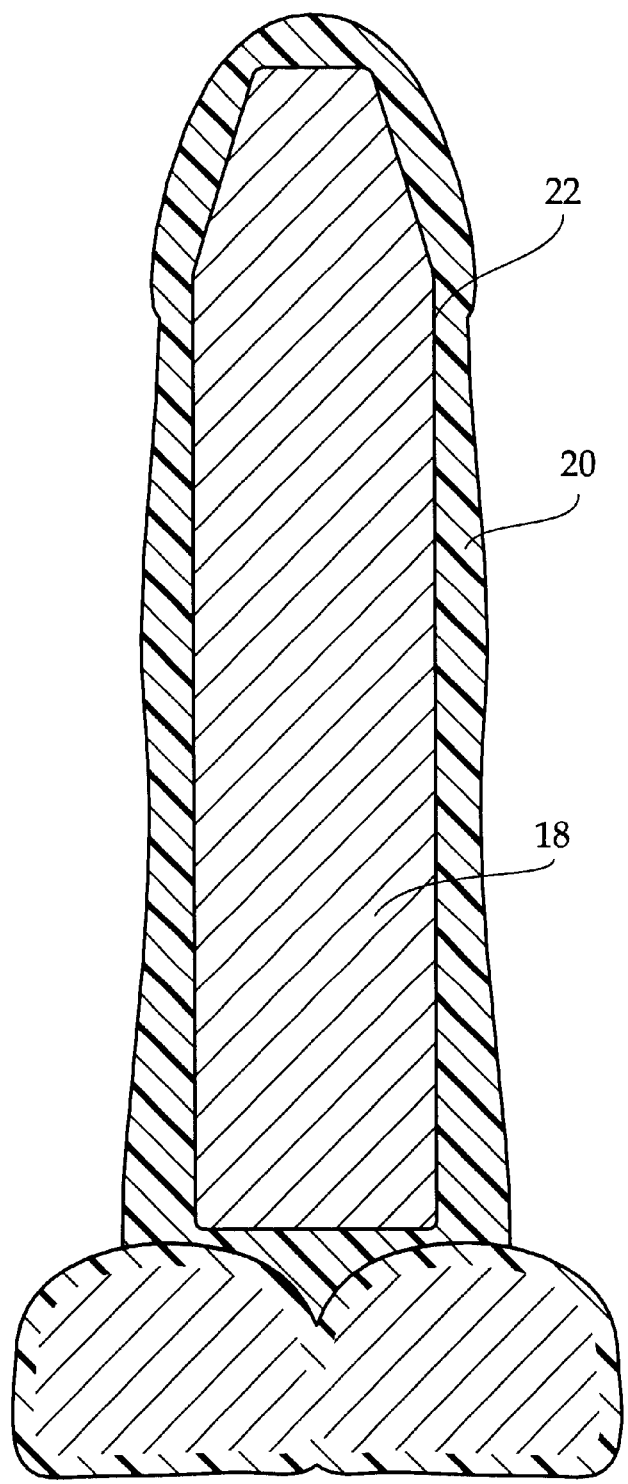
FIG. 2 is a cross sectional view of the sexual aid device with a magnet incorporated therein.

FIG. 1 illustrates a sexual aid device 10, substantially the size and shape of an adult male penis, comprising a head portion 12, an elongated shaft 14, and a base portion 16. The base portion 16 may be used to hold the device 10 when in use. The device further has an outer covering 20 that is constructed from a resilient material, such as rubber or the like, to simulate the look and feel of an erect adult penis. Within the outer covering 20 is a cavity 22.

A magnetic element 18 is housed within the device 10, within the cavity 22, such that the magnetic device 18 is substantially the same size and shape as the cavity 22. The magnet 18 is cylindrical in shape, one piece, and extends continuously substantially from the head portion 12 downward to the base 16. Since it lies below the outer covering 20, the magnet 18 would never come into direct contact with any portion of the human body. Since magnetic field strength decreases with the square of the distance, it is important to bring the actual magnet into as close a position to the human body as possible. Accordingly, the actual thickness of the outer covering 20 should be minimized while maintaining sufficient thickness to ensure comfort for the user.

In use, the head portion 12 is brought into contact with the genital area of the female body. The device 10 may either be rubbed along the outer surface of the vaginal opening or inserted into the vagina for increased pleasure. In either instance, the magnetic attraction caused by bringing the prosthesis 10 into contact with one's sexual organ will induce the blood vessels located therein to fill with blood, thus heightening sexual pleasure, and having as yet unstudied and unrealized benefits to the user's health and well being.

It should be noted that the prefered shape is that of the male penis. However, other suitable cylindrical shapes may be employed, including those that do not necessarily have a "head" which is similar to one found on the male penis. Such shapes are contemplated as being a part of the claimed invention.

In conclusion, herein is presented a sexual aid device with a magnetic source incorporated therein. The invention is illustrated by example in the drawing figures, and throughout the written description. It should be understood that numerous variations are possible, while adhering to the inventive concept. Such variations are contemplated as being a part of the present invention.

What is claimed is:

1. A sexual aid device, comprising:

an outer covering having a head portion, an elongated shaft, and a base portion, the outer covering fabricated to be sized and configured in the shape of an erect human penis; and a magnet, constructed as one piece, extending substantially from the head portion to the base portion.

2. The sexual aid device as recited in claim 1, having a cavity located within the other covering, extending from the head portion to the base portion, wherein the magnet is sized to fit within the cavity.

3. The sexual aid device as recited in claim 2, wherein the outer covering is constructed from a resilient material to simulate an erect penis.

4. A method of using a sexual aid device, said sexual aid device having an elongated shaft, a base portion, and a magnet incorporated within the elongated shaft, comprising the following steps:

holding the sexual aid device at the base portion;

inserting the head portion and the elongated shaft into a user's vaginal opening by said user, thereby bringing the magnet into indirect contact with one's blood vessels, thus bringing heightened sexual pleasure and health benefits to the user.

* * * * *